(12) United States Patent
Côté et al.

(10) Patent No.: US 7,652,148 B1
(45) Date of Patent: Jan. 26, 2010

(54) ELECTROPHILIC AROMATIC SUBSTITUTION WITH DIACYL IMIDAZOLIUM

(75) Inventors: Adrien Pierre Côté, Clarkson (CA); Matthew A. Heuft, Oakville (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 12/202,045

(22) Filed: Aug. 29, 2008

(51) Int. Cl.
*C07D 403/10* (2006.01)
*C07D 403/12* (2006.01)
*A61K 31/4174* (2006.01)

(52) U.S. Cl. .................................. 548/312.7; 514/385
(58) Field of Classification Search .............. 548/312.7; 514/385
See application file for complete search history.

(56) References Cited

U.S. PATENT DOCUMENTS

| 5,476,968 | A | 12/1995 | Imai et al. |
| 7,122,700 | B2 | 10/2006 | Bender et al. |
| 7,271,290 | B2 | 9/2007 | Murphy et al. |

OTHER PUBLICATIONS

Nakano et al., "Synthesis and Intramolecular Magnetic Interaction of Triphenylamine Derivatives with Nitronyl Nitroxide Radicals", Polyhedron 24, 2141-2147 (2005).*

Oelschläger et al., "Ergiebige Synthese des 10-Methylphenothiazin-3,7-dicarbaldehyds (Productive Shynthesis of 10-Methylphenothiazin-3,7-dicarbaldehyde)", Arch. Pharm. (Weinheim) 320, 37-381 (1987).

Bergman et al., "Synthesis of Aromatic Aldehydes via 2-Aryl-N,N'-Diacryl-4- Imidazolines", Tetrahedron 36, 2505-2511 (1980).

* cited by examiner

*Primary Examiner*—Kamal A Saeed
*Assistant Examiner*—Janet L Coppins
(74) *Attorney, Agent, or Firm*—Pillsbury Winthrop Shaw Pittman LLP

(57) ABSTRACT

Polyimidazoline molecules and methods of making them are provided. A representative polyimidazoline has a structure:

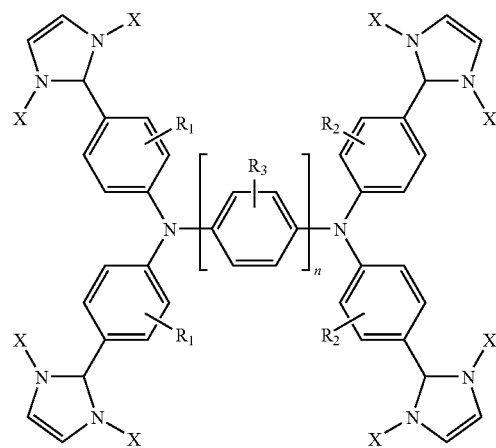

wherein:
X is trifluoroacetyl or trifluoromethanesulfonyl; $R_1$, $R_2$, and $R_3$ are each independently selected from a hydrogen, $C_1$-$C_4$ alkyl, $C_3$-$C_7$ cyclic alkyl, $C_1$-$C_4$ alkoxy, alcohol, and halogen; and n is 1 to 3.

24 Claims, 3 Drawing Sheets

ELECTROPHILIC AROMATIC SUBSTITUTION WITH DIACYL IMIDAZOLIUM

FIELD OF INVENTION

The invention relates generally to polyfunctionalized aromatic amine molecules and methods of making them. Polyfunctionalized aromatic amine molecules find use as hole transport molecules (HTMs) or for other applications requiring functionalized arylamine molecules. Such molecules are used in imaging members, such as layered photoreceptor devices.

INTRODUCTION

In electrophotography, also known as xerography, electrophotographic imaging or electrostatographic imaging, the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. Charge generated by the photoactive pigment move under the force of the applied field. The movement of the charge through the photoreceptor selectively dissipates the charge on the illuminated areas of the photoconductive insulating layer while leaving behind an electrostatic latent image. This electrostatic latent image may then be developed to form a visible image by depositing oppositely charged particles on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

Typical multilayered photoreceptors have at least two layers, and may include a substrate, a conductive layer, an optional charge blocking layer, an optional adhesive layer, a photogenerating layer (sometimes referred to as, and used herein interchangeably, a "charge generation layer," "charge generating layer," or "charge generator layer"), a charge transport layer, an optional overcoating layer and, in some embodiments, an anticurl backing layer. In the multilayer configuration, the active layers of the photoreceptor are the charge generating layer (CGL) and the charge transport layer (CTL).

As more advanced, higher speed electrophotographic copiers, duplicators and printers were developed, however, degradation of image quality was encountered during extended cycling. The complex, highly sophisticated duplicating and printing systems operating at very high speeds have placed stringent requirements, including narrow operating limits, on the imaging members. Thus, photoreceptor materials are required to exhibit, not only efficient charge generation and charge transport properties, but also structural integrity and robustness so as to withstand mechanical abrasion during image development cycles.

Routine mechanical wear impairs the performance of photoreceptors in xerographic devices. To abate such wear, protective overcoat layers (OCLs) are typically added to photoreceptor layers. Overcoat layers comprise cross-linked polymers and thus impart greater mechanical robustness. To maintain the charging ability of the a photoreceptor layer with an overcoat layer, hole transport molecules (HTMs) are cross-linked to overcoat layers. Covalent cross-linking between HTMs and polymers and/or HTMs requires a reactive functional group on the HTM. Aldehyde (i.e. formyl) groups are one of the most valuable because aldehyde groups can be transformed into many other species that can covalently cross-link within OCLs. One commonly used transformed species for OCLs is an aromatic hydroxymethyl group, obtained from the reduction of aldehyde moieties.

Alternatively, non-covalent crosslinking may occur between aldehyde functional groups (a polarizablable electrophile) and derivatives of aldehyde functional groups. In terms of non-bonding intermolecular interactions aldehydes or their derivatives—are generally dipolar species which can interact with other dipolar species. Additionally, aldehydes and their derivatives may participate in hydrogen bonding.

The introduction of a formyl (aldehyde; —CHO) group to aromatic molecules by way of a Vilsmeier-Haack (VH) reagent requires high temperatures and long reaction times. VH reagents pose problems for scale-up due to their high viscosity, potential violent reactivity, corrosive nature, numerous decomposition pathways and isolation of desired products from VH reagents requires labor-intensive work-ups that involve use of large quantities of solvent.

SUMMARY

The invention provides formylation methods which, in various embodiments, are more efficient, less expensive, more versatile, and safer than state-of-the-art VH methodology and other formylation methods. The invention also provides intermediates of diacyl imidazolium substituted molecules.

In an embodiment of the invention methods and intermediates, an N,N'-bis(trifluoroacetyl)imidazolium reagent is used to introduce imidazoline groups onto aromatic ring moieties such as those found in tetraphenylalrylenediamines-based hole transport molecules (HTMs). The process is used to make intermediates for preparing crosslinkable HTMs, which can be used in photoreceptor overcoat layers. Subsequent hydrolysis of bis(trifluoroacetyl)imidazolium moieties with mild acid yields aldehyde (formyl) functionalized HTMs. Various embodiments of the methods afford high yield (>80%) of tetra-formylated HTM, or an 11-fold improvement in yield over Vilsmeier-Haack chemistry. Furthermore, a method amenable for adapting the chemistry to larger scale batch reactions has been established. The invention method is an alternative to the VH method and other methods, offering significant cost reduction as well as improved safety and reduced solvent use.

According to one embodiment, there are provided novel processes for the formylation of polyaromatic amine molecules. In one embodiment, polyaromatic diamine molecules are formylated via electrophillic addition of diacyl imidazolium reagent and subsequent hydrolysis. In another embodiment, imidazoline intermediates are isolated and serve as protected formyl groups prior to hydrolysis. In another embodiment, the process is carried out in single reaction vessel.

DETAILED DESCRIPTION

Figure 1:
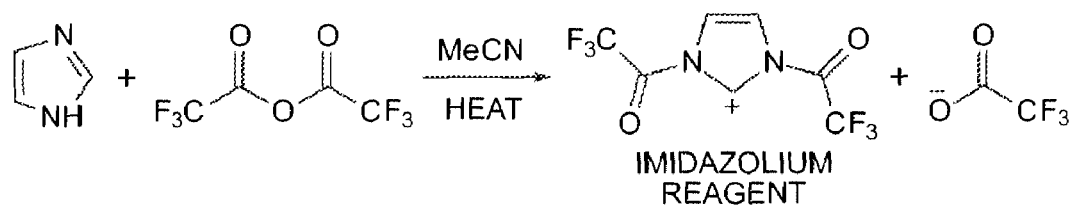
FIG. 1 shows the preparation of a diacyl imidazolium reagent.
Figure 2:
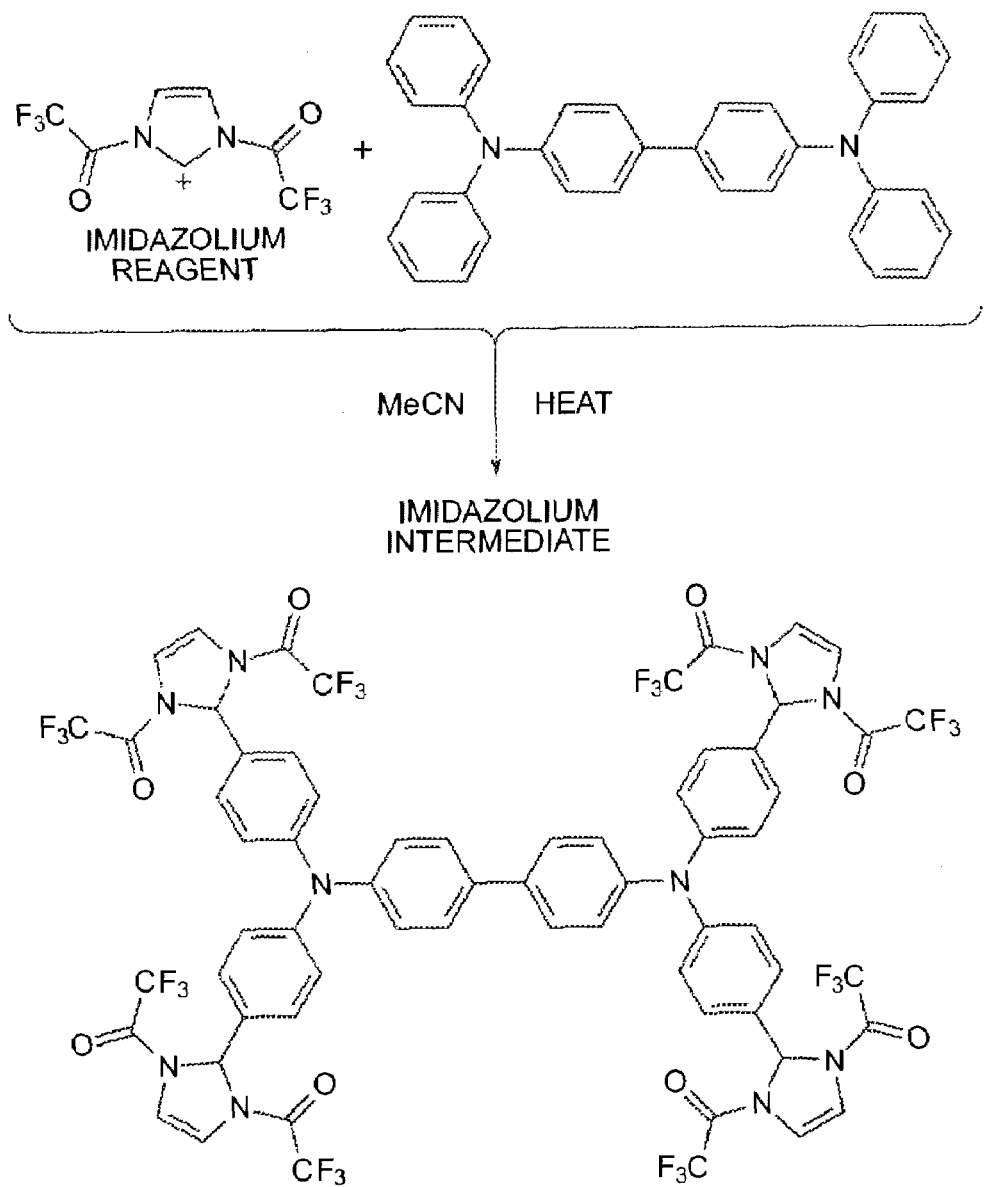
FIG. 2 shows the preparation of imidazoline intermediate.
Figure 3:
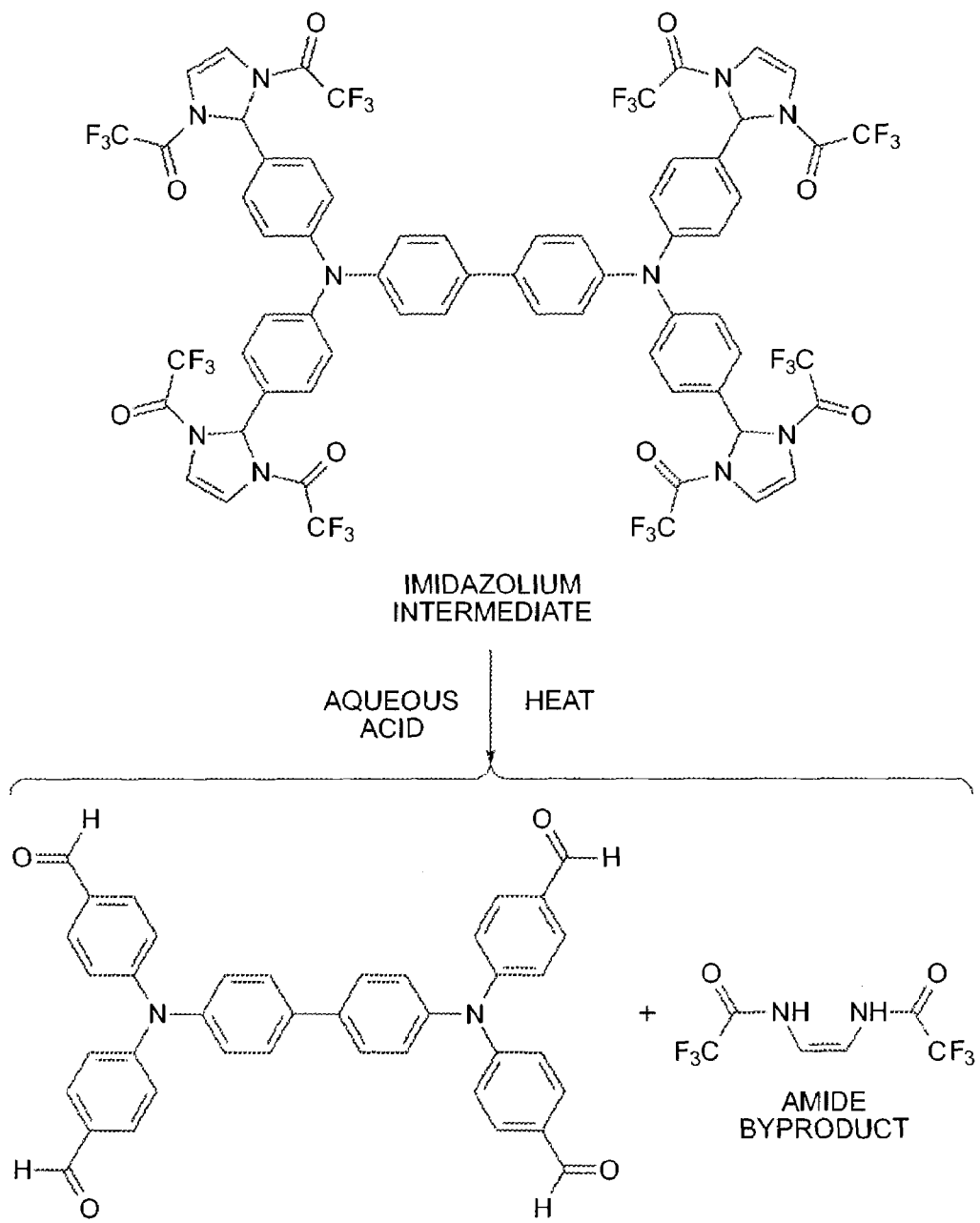
FIG. 3 shows the preparation of a tetra-formylated HTM.

A method of the invention installs multiple reactive diacyl imidazoline groups onto one molecule. Diacyl imidazoline groups are masked aldehydes. Aldehydes are versatile functional groups in organic chemistry in the sense that they may be converted to many other types of functional groups. Non-limiting examples of such other functional groups include acetals, amides, anhydrides, carboxylic acids and esters, gem-dihalides, episulfides, epoxides, halo alcohols and ethers, ketones, nitrites, oximes, and alcohols.

Polyformylated hole transport molecules (HTMs) are also precursors to HTMs with benzylhydroxy groups. Benzylhydroxyl HTMs are prepared by chemical reduction of formyl moieties (aldehyde or CHO) of polyformylated HTMs.

HTMs with hydroxyl groups can react with polymers and/or with other HTMs with hydroxyl groups to become chemically attached to, or within, photoreceptor overcoat layers.

The polyformylated materials and methods of making them described herein are useful for applications beyond photoreceptors and HTMs. The materials disclosed herein and the methods used to make them are applicable to any device which incorporates polyformylated materials or materials derived from polyformylated materials. Non-limiting examples of such devices include light emitting diodes, field effect transistors, solar cells, printed electronics, semiconductors, electrodes, sensors, and photoconductors.

The term "polyimidazoline compound" as used herein refers to a compound in which an aromatic hydrogen atom of an aryl amine has been replaced by a diacyl imidazolium moiety. Without being bound by theory, the process which replaces aromatic hydrogen is an electrophilic aromatic substitution. Hydrogen replacement will generally occur at the position para to the amine nitrogen at each aromatic ring. Established rules predict the regiochemistry of electrophilic attack on aromatic carbon hydrogen bonds.

Examples of polyimidazoline molecules include, but are not limited to compounds having formula,

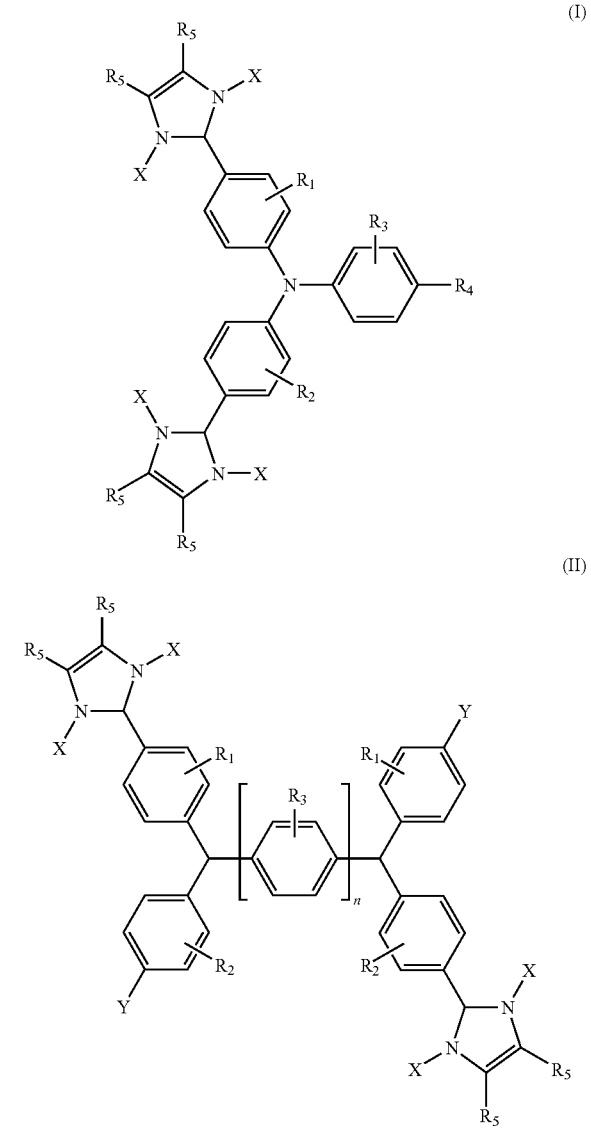

in which X is an acyl, for example, trifluoroacetyl, trichloroacetyl, tribromoacetyl, acetyl, or a sulfonyl, for example, methanesulfonyl, tolylsulfonyl, mesitylsulfonyl, trifluoromethanesulfonyl, tri chloromethanesulfonyl, or trichloromethanesulfonyl.

The group Y in structure II can be a $C_1$-$C_5$ alkyl, for example methyl, ethyl, propyl, butyl, and branched isomers. Y can also be $C_3$-$C_7$ cyclic alkyl, $C_1$-$C_4$ alkoxy, hydroxyl, ω-hydroxy-substituted $C_2$-$C_8$ alkyl or an aryl, for example, phenyl, or a substituted phenyl, for example tolyl.

In another embodiment, the group Y can be an imidazoline moiety having structure:

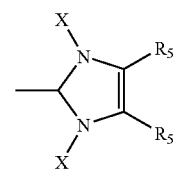

In this embodiment, $R_5$ can be hydrogen, $C_1$-$C_5$ alkyl, $C_3$-$C_7$ cyclic alkyl, for example cyclopropyl, cyclobutyl, cyclopentyl, cyclohexyl, and cycloheptyl. $R_4$ can also be a halogen, a nitro, an alcohol, an amide, and an amine. In yet another embodiment, two adjacent $R_5$ moieties on the same imidazole can represent a fused benzene ring, thus forming a benzimidazole, optionally substituted with $C_1$-$C_5$ alkyl, $C_3$-$C_7$ cyclic alkyl, halogen, nitro, alcohol, amide, and amine.

The groups $R_1$, $R_2$, and $R_3$ in structures I and II can each be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl, halogen, and aryl optionally substituted with $C_1$-$C_5$ alkyl. The group $R_4$ in structure I can each independently be $C_1$-$C_5$ alkyl, hydroxy, ω-hydroxy-substituted $C_2$-$C_8$ alkyl, halogen, or aryl wherein the aryl can be substituted with $C_1$-$C_5$ alkyl. The subscript "n" in structure II can be 1 to 3, designating the number of linking arylene units between amine nitrogens. The group $R_3$ in structure II can each independently be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl, halogen, and aryl optionally substituted with $C_1$-$C_5$ alkyl. The phase "each independently" means that each arylene unit substituted with $R_3$ may have a different $R_3$ substituents chosen from hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl, halogen, and aryl optionally substituted with $C_1$-$C_5$ alkyl.

Other examples of polyimidazoline molecules include, but are not limited to the structures:

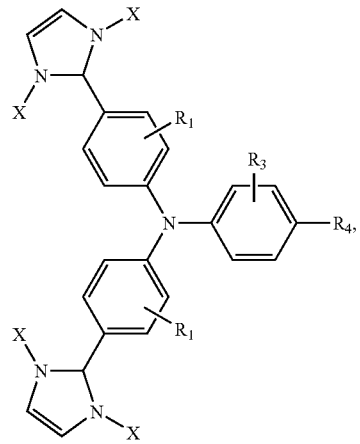

-continued

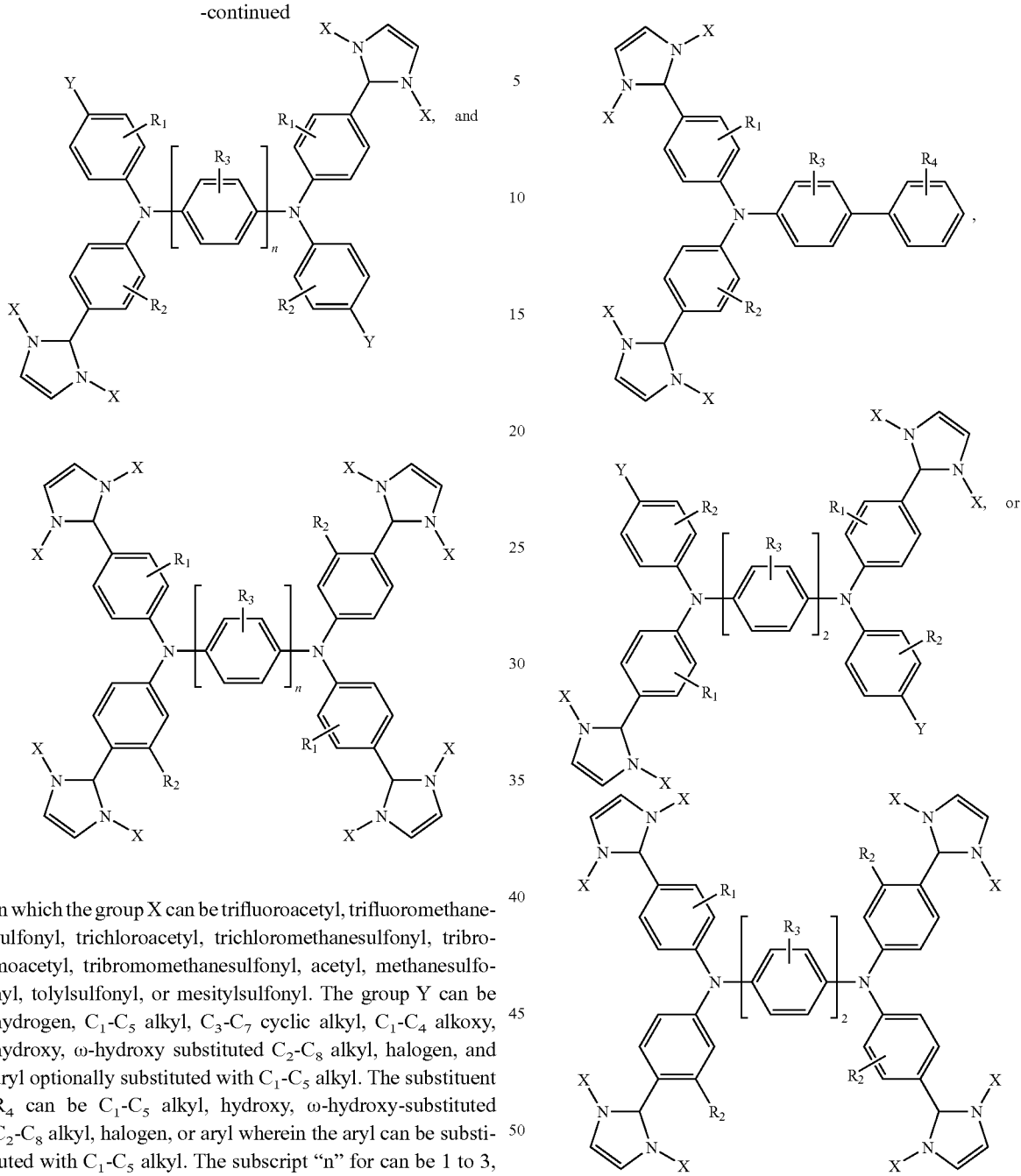

in which the group X can be trifluoroacetyl, trifluoromethanesulfonyl, trichloroacetyl, trichloromethanesulfonyl, tribromoacetyl, tribromomethanesulfonyl, acetyl, methanesulfonyl, tolylsulfonyl, or mesitylsulfonyl. The group Y can be hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, and aryl optionally substituted with $C_1$-$C_5$ alkyl. The substituent $R_4$ can be $C_1$-$C_5$ alkyl, hydroxy, ω-hydroxy-substituted $C_2$-$C_8$ alkyl, halogen, or aryl wherein the aryl can be substituted with $C_1$-$C_5$ alkyl. The subscript "n" for can be 1 to 3, designating the number of linking arylene units between amine nitrogens. The substituent(s) $R_3$ can each independently be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl, halogen, and aryl optionally substituted with $C_1$-$C_5$ alkyl. The term "each independently" means that each arylene 1 to n is substituted with $R_3$ may have a different $R_3$ substituents chosen from hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl, halogen, and aryl optionally substituted with $C_1$-$C_5$ alkyl.

Other non-limiting examples of polyimidazoline molecules according to the invention include, for example, molecules having a structure:

in which X is trifluoroacetyl, Y is $C_1$-$C_5$ alkyl or is aryl optionally substituted with $C_1$-$C_5$ alkyl. $R_1$, $R_2$, $R_3$, and $R_4$ are each independently hydrogen, $C_1$-$C_5$ alkyl, $C_3$-$C_7$ cyclic alkyl, $C_1$-$C_4$ alkoxy, hydroxyl, ω-substituted $C_2$-$C_8$ alkyl, atoms, alcohol, and halogen, or aryl optionally substituted with $C_1$-$C_5$ alkyl. The term "each independently" means for example that each $R_3$ substituent on different arylene units may have a different $R_3$ substituents chosen from hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl, halogen, and aryl optionally substituted with $C_1$-$C_5$ alkyl.

Additional examples of polyimidazoline molecules according to the invention include, for example, molecules having a structure:

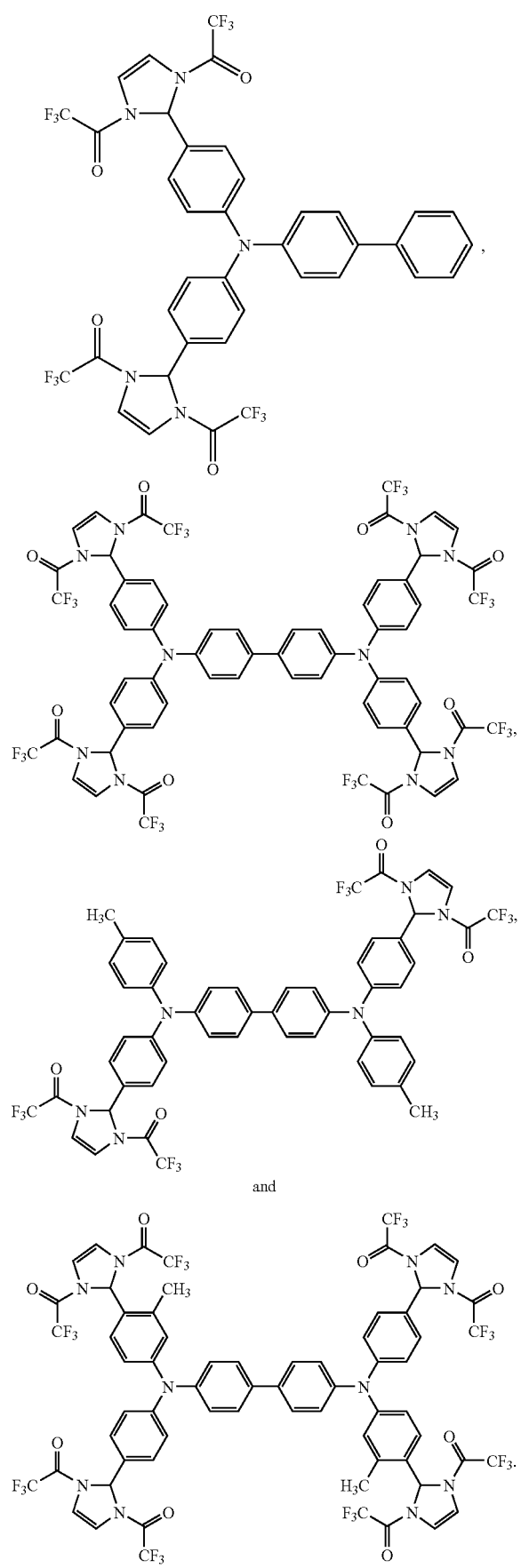

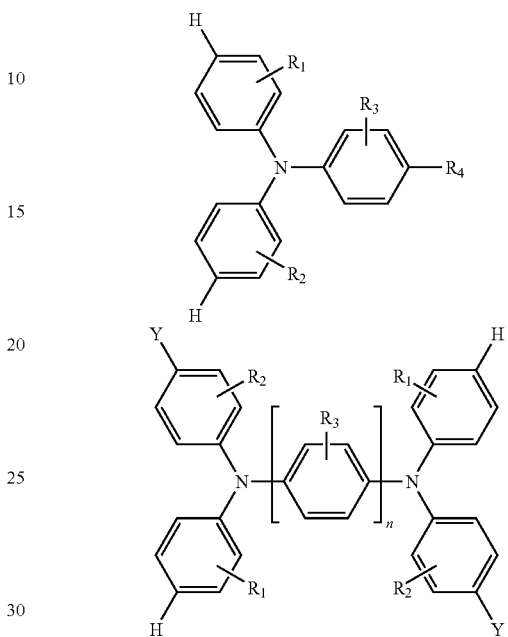

In another embodiment, the invention provides a chemical process including the steps: (a) charging a vessel or container with a mixture comprising imidazole, trifluoroacetic anhydride, and one of a compound having the following structures A or B respectively in which the substituent Y can be hydrogen, $C_1$-$C_5$ alkyl, $C_3$-$C_7$ cyclic alkyl, $C_1$-$C_4$ alkoxy, hydroxy, ω-substituted $C_2$-$C_4$-alkyl, halogen or aryl optionally substituted with $C_1$-$C_5$ alkyl. The substituents $R_1$, $R_2$, and $R_3$ can independently be hydrogen, $C_1$-$C_5$ alkyl, $C_3$-$C_7$ cyclic alkyl, $C_1$-$C_4$ alkoxy, hydroxy, ω-substituted $C_2$-$C_4$-alkyl, halogen or aryl optionally substituted with $C_1$-$C_5$. The substituent $R_4$ is hydrogen, $C_1$-$C_5$ alkyl, $C_3$-$C_7$ cyclic alkyl, $C_1$-$C_4$ alkoxy, hydroxy, ω-substituted $C_2$-$C_4$-alkyl, halogen or aryl optionally substituted with $C_1$-$C_5$ alkyl. The subscript "n" in structure B can be 1 to 3, designating the number of linking arylene units between amine nitrogens. The term "each independently" means for example that each $R_3$ substituent on different arylene units may have a different $R_3$ substituents chosen from hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl, halogen, and aryl optionally substituted with $C_1$-$C_5$ alkyl.

The next step (b) is heating the mixture in a non aqueous solvent. Suitable non aqueous solvents include but are not limited to acetonitrile, tetrahydrofuran, diethylether, diisopropylether, dichloromethane, chloroform, propionitrile, dioxane, dioxolane, tetrahydropyran, dimethoxyethane, glymes, nitromethane, ethyl acetate, propyl acetate, acetone, methylethylketone, methyl isobutyl ketone, acetic acid, trifluoroacetic acid, trifluoroacetic anhydride, acetic anhydride, alkanes or the like. The mixture is heated for a period of 40 to 120° C. or until the compound A or B is consumed; the next step (c) is quenching the reaction with water to precipitate a polyimidazoline molecule The term "non aqueous" solvent as used herein refers to a solvent such as nitriles (e.g., acetonitrile, proprionitrile, benzonitrile). Other suitable solvents include tetrahydrofuran, diethylether, diisopropylether, dichloromethane, chloroform, dioxane, dioxolane, tetrahydropyran, dimethoxyethane, glymes, nitromethane, ethyl acetate, propyl acetate, acetone, methylethylketone, methyl isobutyl ketone, acetic acid, trifluoroacetic acid, trifluoroacetic anhydride, acetic anhydride, and alkanes. Certain polar, non aqueous solvents dissolve polar compounds like amines and may be dried to remove traces of water.

The examples exemplify, but are not intended to limit, the methods of the invention. According to one embodiment, a standard reaction vessel or container such as glassware may be employed. In other embodiments, such as those employed in larger scale reaction, non-glass reactor vessels or containers can be used. In each case, stirring or agitation, for example, via magnetic or mechanical stirring, is used to mix the reactants.

According to one embodiment, trifluoroacetic anhydride and imidazole may be pre-mixed before adding diamine. In this embodiment, acetonitrile solvent and trifluoroacetic anhydride are first combined in a suitable reaction vessel or container. A second solution of imidazole in acetonitrile is added slowly (e.g., drop-wise) to the solution of trifluoroacetic anhydride or triflic anhydride. After addition is complete, the mixture is heated to reflux and monitored (e.g., by HPLC). Consumption of starting imidazole is conveniently followed (e.g., HPLC), and after most or all of the imidazole is consumed, a suitable tetraphenylarylenediamine, for example, tetraphenylbiphenyl diamine is added and the resulting yellow suspension is stirred at reflux for a period of about 16 hours. Reaction progress may be followed using, for example, HPLC. After monitoring showed complete consumption of diamine, the reaction is quenched with water and stirred for a period of about 1 hour, during which a yellow precipitate forms and is conveniently isolated by filtration. Analysis shows a greater than about 99% yield or essentially complete theoretical yield of polyimidazoline compound.

The trifluoroacetyl moiety is analogous to an acetyl moiety wherein each methyl hydrogen is replaced by a more electronegative fluorine atom. The trifluoroacetyl moiety is an example of a perhalogenated acyl. Other haloacyl include chloroacetyls, pentafluoropropionic anhydride and other partially and perhalogenated acyls.

A trifluoromethylsulfonyl moiety is analogous to a trifluoromethylacetate wherein the carbonyl (C=O) moiety is replaced by a sulfonyl (SO$_2$) moiety. The trifluoromethylsulfonic moiety can be referred to as a triflate moiety. Thus triflate anhydride is an alternative formation of a reactive bistriflate imidazolium reagent.

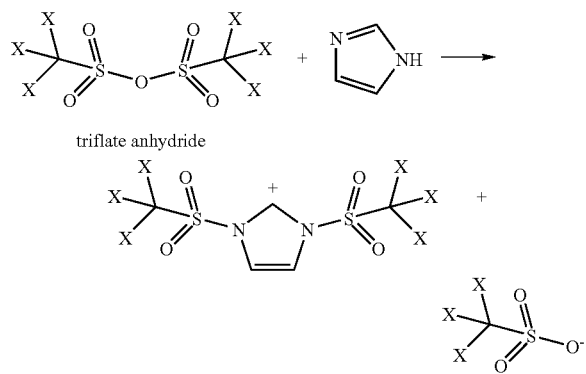
triflate anhydride

According to another embodiment, trifluoromethylsulfonic anhydride (triflic anhydride) may be used in place of trifluoromethylsulfonic acid.

Benzimidazole may replace imidazole one-to-one in formulating diacyl imidazolium reagents for treating of tetraphenylarylenediamines. Thus an additional embodiment are trifluoroacetyl benzimidazolium reagents for use in the electrophilic substitution of aromatic CH bonds. Substituted imidazole compounds may also replace imidazole. Suitable substituted imidazoles and benzimidazoles include, for example:

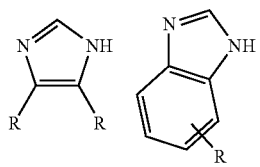

wherein R is selected from the group consisting of $C_{1-5}$ alkyl, cyclic $C_{3-7}$ alkyl, halogen, nitro, alcohol, amide, and amine.

In one embodiment of the invention, reactive aryl hydrogens may be blocked by the inclusion of substituents. Introduction of such blocking groups promotes site-selective formylation of only desired sites. A non-limiting example of a mono-amine having a blocked aromatic C—H bond is a compound having structure:

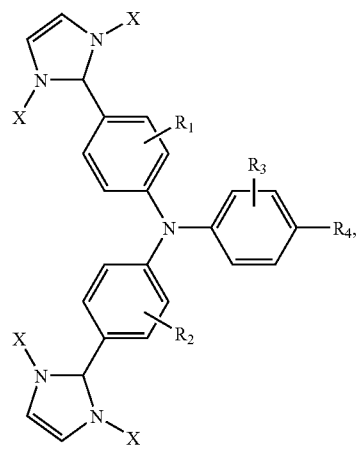

in which groups $R_1$, $R_2$, and $R_3$ can be $C_1$-$C_5$ alkyl, $C_3$-$C_7$ cyclic alkyl, $C_1$-$C_4$ alkoxy, hydroxy, ω-substituted $C_2$-$C_4$ alkyl, halogen or aryl optionally substituted with $C_1$-$C_5$. The substituent $R_4$ is group which replaces a hydrogen which would otherwise react under conditions of electrophillic aromatic substitution. The presence of substituent $R_4$ allows introduction of imidazolium moiety only at the two aryl CH bonds disposed para- to the amine nitrogen. Non-limiting examples of R4 include but are not limited to $C_1$-$C_5$ alkyl, $C_3$-$C_7$ cyclic alkyl, hydroxy, ω-substituted $C_2$-$C_4$-alkyl, halogen or aryl optionally substituted with $C_1$-$C_5$ alkyl.

Non-limiting examples of diamines having a blocked aromatic C—H bond is a compound having structure:

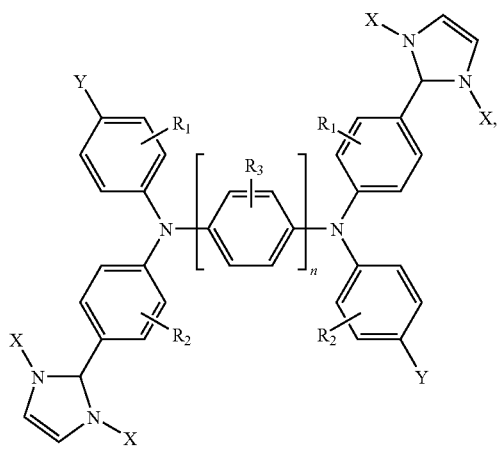

in which Y is $C_1$-$C_5$ alkyl, for example methyl, ethyl, propyl, butyl, and branched isomers. Y can also be an aryl, for example, phenyl, or a substituted phenyl, for example tolyl. Y can also be ω-hydroxy-substituted alkyl groups wherein the alkyl group has at least 2 to about 8 carbon atoms. The substituent Y replaces a hydrogen which would otherwise react under conditions of electrophillic aromatic substitution. The presence of substituent Y allows introduction of imidazolium moiety only at the two aryl CH bonds disposed para- to the amine nitrogen.

Diamine compounds of the invention having blocking groups for the selective formylation may be synthesized according to the following general scheme:

Here blocking groups are introduced as part of an amine precursor which is then coupled with an arylene linker affording a diamine HTM.

The term "tetraphenylbiphenyl diamine" as used herein refers to a molecule having two amino moieties separated by a biphenyl spacer. Tetraphenylbiphenyl diamines have two terminal phenyl groups attached to each nitrogen. Tetraphenybiphenyl diamines according to the invention have aromatic hydrogen atoms which react with bistrifluoracetyl-imidazole via electrophilic aromatic substitution.

Tetraphenylbiphenyl diamines include compounds having a structure:

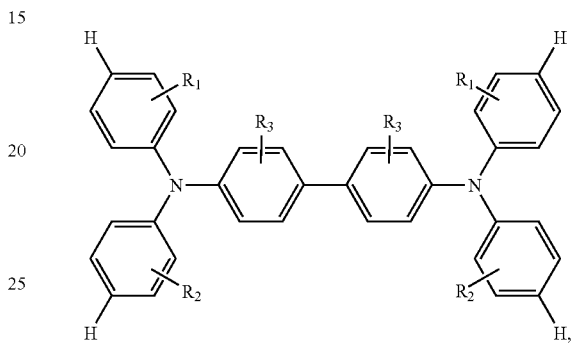

in which substituent variables $R_1$, $R_2$, and $R_3$ are each independently hydrogen, $C_1$-$C_5$ alkyl, $C_3$-$C_7$ cyclic alkyl, $C_1$-$C_4$ alkoxy, ω-hydroxy substituted $C_2$-$C_8$ alkyl, halogen, and aryl

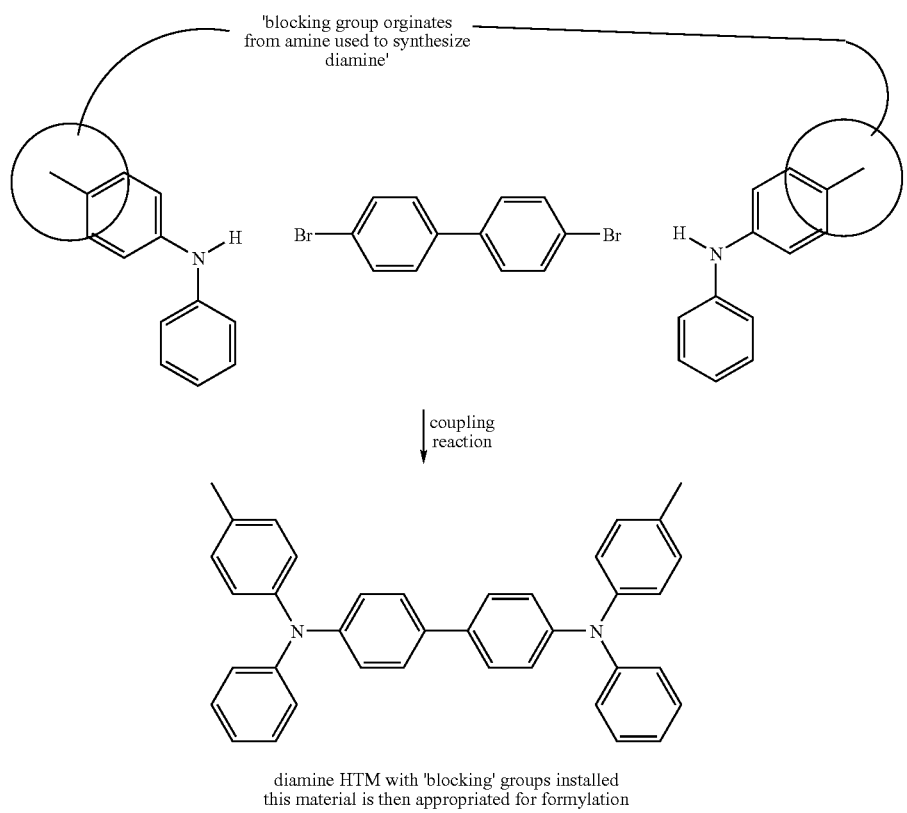

diamine HTM with 'blocking' groups installed
this material is then appropriated for formylation optionally substituted with $C_1$-$C_5$ alkyl. Hydrogen atoms on the four terminal phenyl moieties are the site of electrophilic aromatic substitution.

In one embodiment, a tetraphenylbiphenyl diamine has a structure:

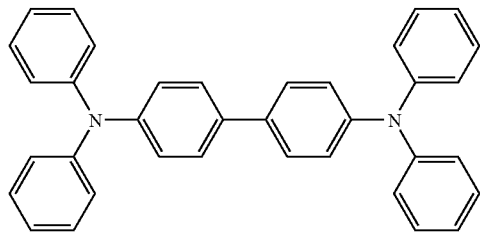

In another embodiment, a mono-amine may be derivatized according to the methods of the invention. Non-limiting examples of mono-amines include:

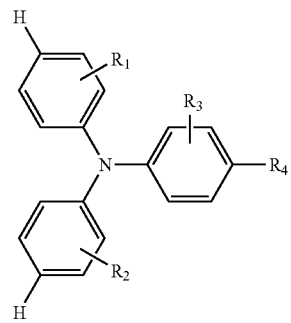

in which substituents $R_1$, $R_2$, and $R_3$ are each independently $C_1$-$C_5$ alkyl, $C_3$-$C_7$ cyclic alkyl, $C_1$-$C_4$ alkoxy, ω-hydroxy substituted $C_2$-$C_8$ alkyl, halogen, and aryl optionally substituted with $C_1$-$C_5$ alkyl. The group $R_4$ can be $C_1$-$C_5$ alkyl, $C_3$-$C_7$ cyclic alkyl, ω-hydroxy substituted $C_2$-$C_8$ alkyl, halogen, and aryl optionally substituted with $C_1$-$C_5$ alkyl.

In another embodiment, diamines can be derivatized having structure:

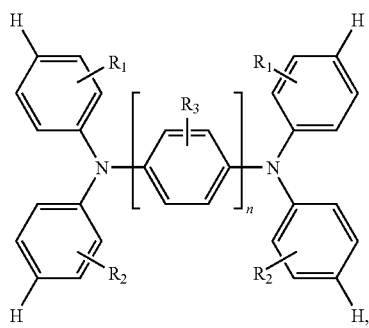

in which substituents $R_1$ and $R_2$ are each independently hydrogen, $C_1$-$C_5$ alkyl, $C_3$-$C_7$ cyclic alkyl, $C_1$-$C_4$ alkoxy, ω-hydroxy substituted $C_2$-$C_8$ alkyl, halogen, and aryl optionally substituted with $C_1$-$C_5$ alkyl. The subscript "n" in can be 1 to 3, designating the number of linking arylene units between amine nitrogens. The groups $R_3$ (up "n" in number) can each independently be selected from hydrogen, $C_1$-$C_5$ alkyl, $C_3$-$C_7$ cyclic alkyl, $C_1$-$C_4$ alkoxy, ω-hydroxy substituted $C_2$-$C_8$ alkyl, halogen, and aryl optionally substituted with $C_1$-$C_5$ alkyl.

Non limiting examples of diamines include compounds having structure:

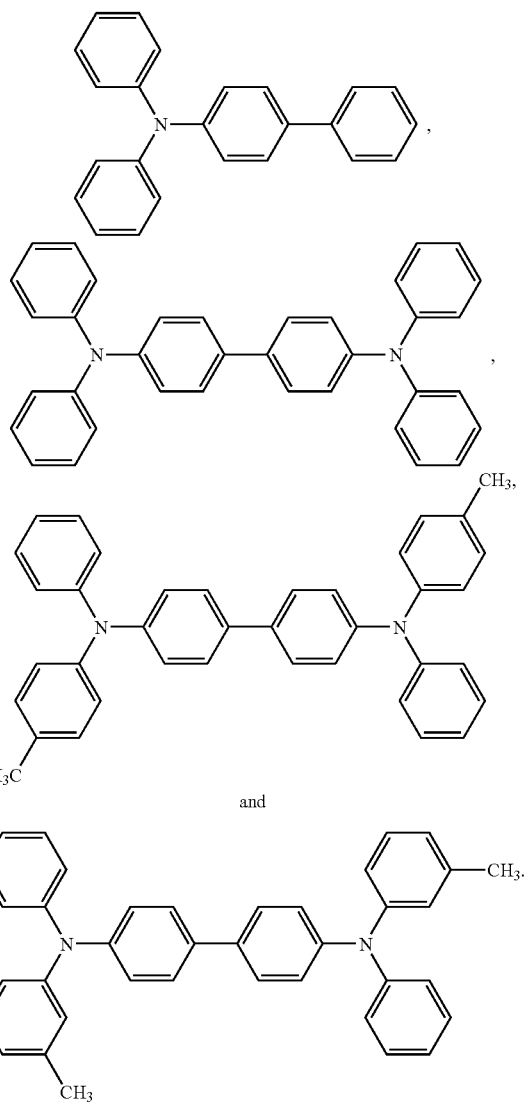

and

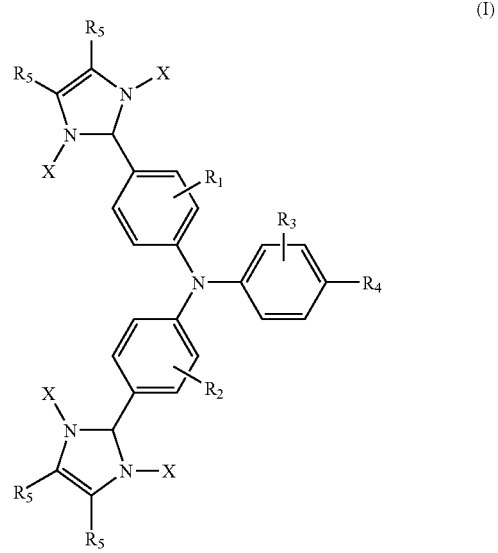

The process of the invention produces polyimidazoline products having structure:

(I)

-continued

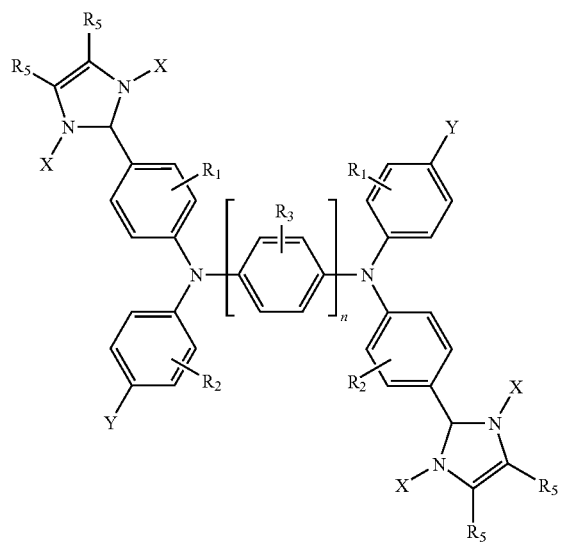
(II)

in which X can be trifluoroacetyl, trifluoromethanesulfonyl, trichloroacetyl, trichloromethanesulfonyl, tribromoacetyl, tribromomethanesulfonyl, acetyl, methanesulfonyl, tolylsulfonyl, or mesitylsulfonyl; Y is $C_1$-$C_5$ alkyl, $C_3$-$C_7$ cyclic alkyl, $C_1$-$C_4$ alkoxy, ω-hydroxy substituted $C_2$-$C_8$ alkyl, halogen, and aryl optionally substituted with $C_1$-$C_5$ alkyl, or an imidazoline having structure:

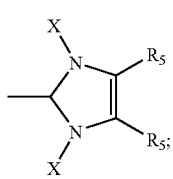

The groups $R_1$, $R_2$, and $R_3$ are each independently hydrogen, $C_1$-$C_5$ alkyl, $C_3$-$C_7$ cyclic alkyl, $C_1$-$C_4$ alkoxy, ω-hydroxy substituted $C_2$-$C_8$ alkyl, halogen, and aryl optionally substituted with $C_1$-$C_5$ alkyl. For structure I (monoamine) $R_4$ can be $C_1$-$C_5$ alkyl, $C_3$-$C_7$ cyclic alkyl, hydroxy, ω-hydroxy substituted $C_2$-$C_8$ alkyl, halogen, and aryl optionally substituted with $C_1$-$C_5$ alkyl. $R_5$ is selected from the group consisting of hydrogen, $C_1$-$C_5$ alkyl, $C_3$-$C_7$ cyclic alkyl, halogen, nitro, alcohol, amide, and amine, or two adjacent $R_4$ moieties on an imidazole represent a fused benzene ring, thus forming a benzimidazole, optionally substituted with $C_1$-$C_5$ alkyl, $C_3$-$C_7$ cyclic alkyl, halogen, nitro, alcohol, amide, and amine n=1 to 3.

In one embodiment, X is trifluoroacetyl. Non-limiting examples of such polyimidazoline compounds include:

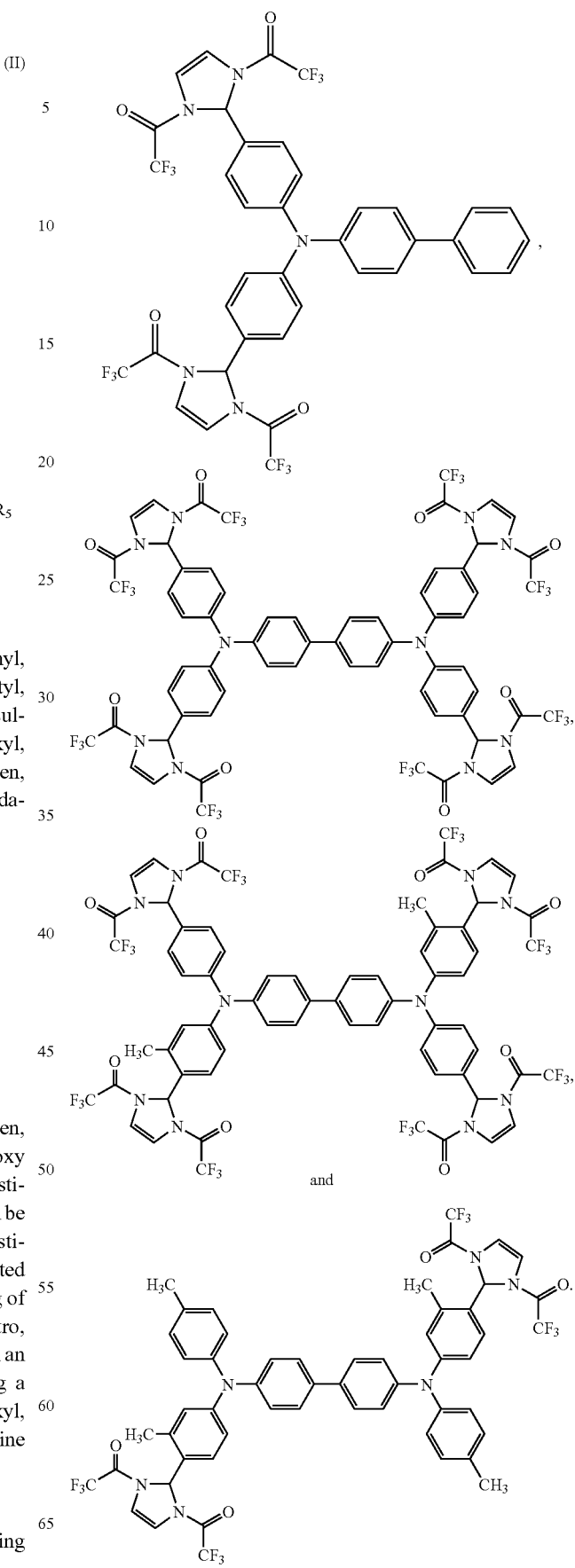

Another embodiment of the invention is a "one-pot" synthesis of polyformylated products without isolation of intermediate imidazoline intermediates. A "one-pot" synthesis according to the invention is advantageous for the following reasons:

Multi-step reactions demand more solvent because intermediates must be isolated and then redissolved in one or more different solvents. A one-pot reaction reduces or eliminates the need for additional solvent(s). Multistep reactions require more operator time than one-pot reactions because of time required to isolate and or to transfer materials between vessels. One-pot reactions are more amenable to large-scale scaling up and reduce production costs. A multi-step reaction is demanding in terms of numerous controls, safety interlocks, equipment needs, operator training. One-pot reactions combine and simplify reaction process engineering.

The process of the invention produces polyformylated product by introducing a hydrolysis step which hydrolyzes the imidazoline moiety releasing the formyl (aldehyde) moiety. In one embodiment, the process includes the steps:

(a) charging a vessel with a mixture comprising imidazole, an acyl or sulfonyl anhydride, and one of a compound having the following structures A or B respectively:

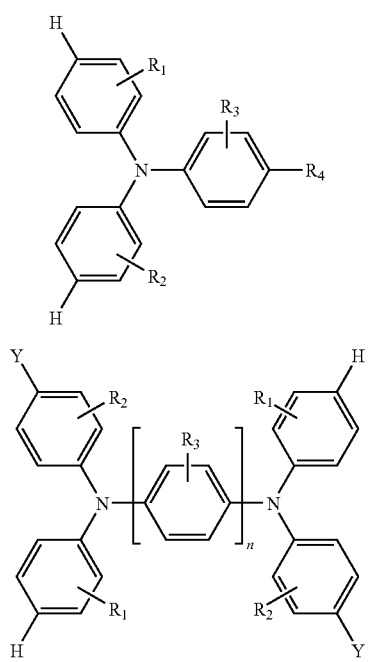

(b) heating the mixture in a polar non aqueous solvent until the compound A or B is consumed;
(c) charging the vessel with an aqueous acid,
(d) heating the mixture in aqueous solvent system until polyimidazoline is consumed.

In one embodiment, compound A has a structure:

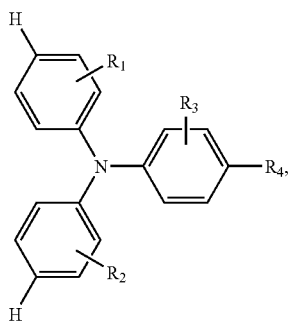

in which $R_1$, $R_2$, and $R_3$ for can each independently be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl. The group $R_4$ can be $C_1$-$C_5$ alkyl, $C_3$-$C_7$ cyclic alkyl, hydroxy, ω-hydroxy-substituted $C_2$-$C_8$ alkyl halogen, or aryl optionally substituted with $C_1$-$C_5$ alkyl.

In another embodiment, compound B has a structure:

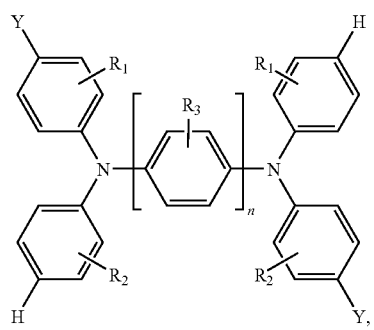

in which group Y can be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl. The substituents $R_1$, $R_2$, and $R_3$ for both A and B can each independently be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl. The group $R_4$ can be $C_1$-$C_5$ alkyl, $C_3$-$C_7$ cyclic alkyl, hydroxy, ω-hydroxy-substituted $C_2$-$C_8$ alkyl halogen, or aryl optionally substituted with $C_1$-$C_5$ alkyl. The variable n for structure can be 1 to 3, designating the number of linking arylene units between amine nitrogens in diamine molecules. Each $R_3$ for structure B can each independently be hydrogen, $C_1$-$C_5$ alkyl, $C_3$-$C_7$ cyclic alkyl, $C_1$-$C_4$ alkoxy, ω-hydroxy-substituted $C_2$-$C_8$ alkyl halogen, or aryl optionally substituted with $C_1$-$C_5$ alkyl.

in which group Y can be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl. The substituents $R_1$, $R_2$, and $R_3$ for both A and B can each independently be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl. The group $R_4$ can be $C_1$-$C_5$ alkyl, $C_3$-$C_7$ cyclic alkyl, hydroxy, ω-hydroxy-substituted $C_2$-$C_8$ alkyl halogen, or aryl optionally substituted with $C_1$-$C_5$ alkyl. The variable n for structure can be 1 to 3, designating the number of linking arylene units between amine nitrogens in diamine molecules. Each $R_3$ for structure B can each independently be hydrogen, $C_1$-$C_5$ alkyl, Non-limiting examples of amines which can be selectively formylated include:

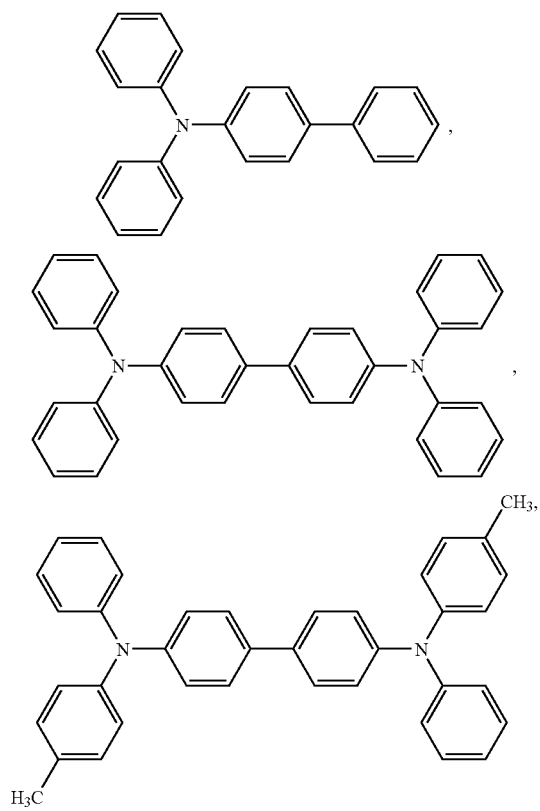

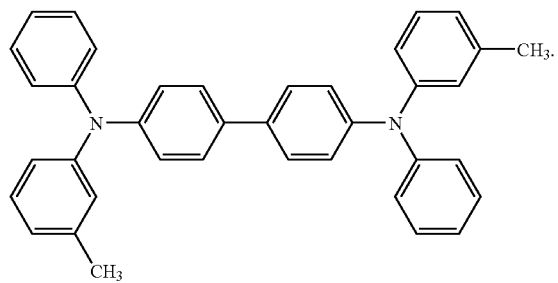

Non-limiting examples of polyformylated products which can be obtained include:

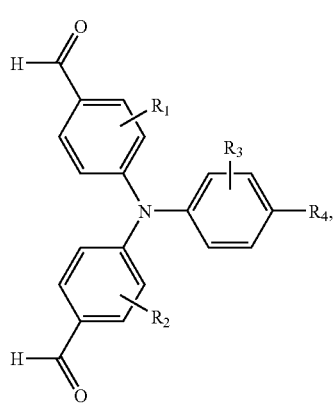

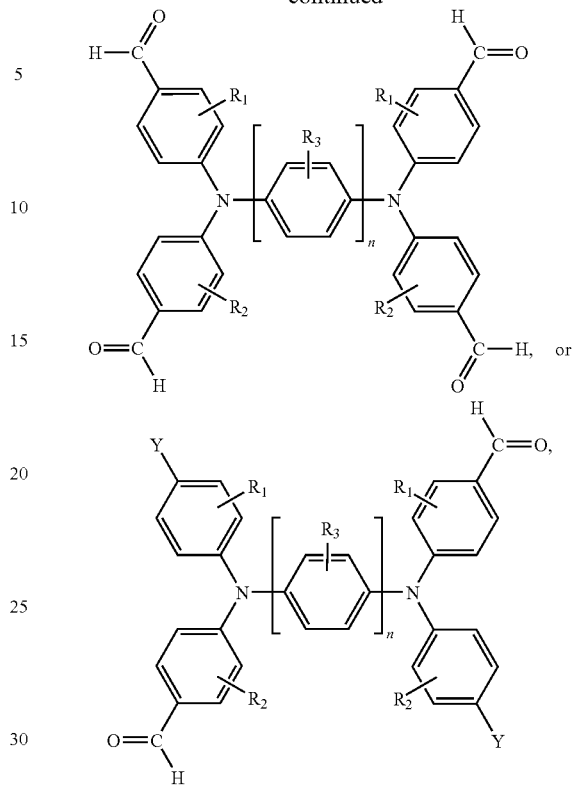

in which group Y can be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl. The substituents $R_1$, $R_2$, and $R_3$ for both A and B can each independently be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl. The group $R_4$ can be $C_1$-$C_5$ alkyl, $C_3$-$C_7$ cyclic alkyl, hydroxy, ω-hydroxy-substituted $C_2$-$C_8$ alkyl halogen, or aryl optionally substituted with $C_1$-$C_5$ alkyl. The variable n for structure can be 1 to 3, designating the number of linking arylene units between amine nitrogens in diamine molecules. Each $R_3$ for structure B can each independently be hydrogen, $C_1$-$C_5$ alkyl, $C_3$-$C_7$ cyclic alkyl, $C_1$-$C_4$ alkoxy, hydroxy, ω-hydroxy-substituted $C_2$-$C_8$ alkyl halogen, or aryl optionally substituted with $C_1$-$C_5$ alkyl.

Other non-limiting examples of polyformylated products according to the invention The process of claim 14 wherein the polyformylated product have structure:

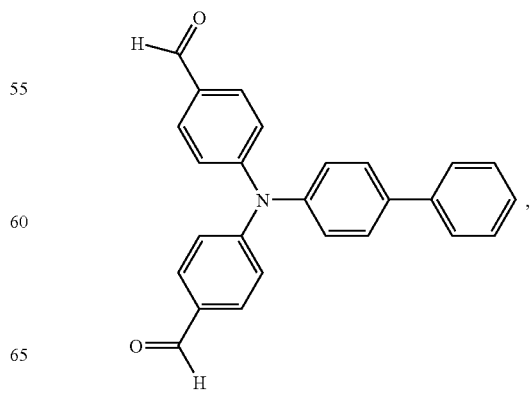

-continued

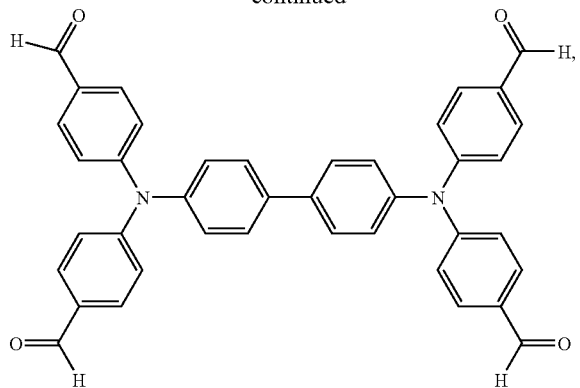

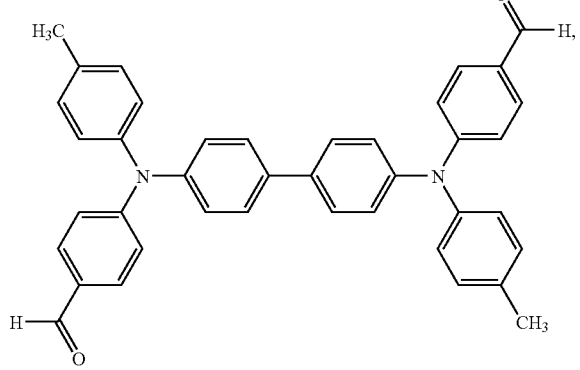

and

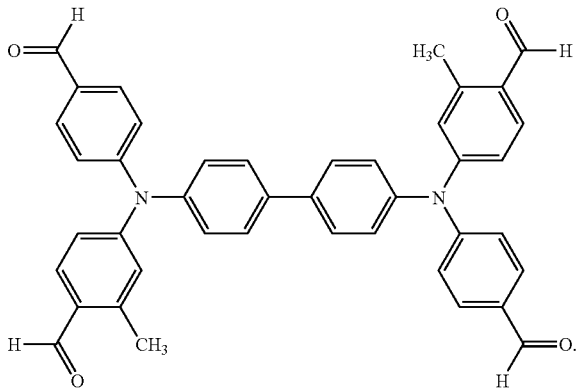

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to an "compound," a "product" or an "intermediate" includes a plurality of compounds, products or intermediates, and so forth.

As used herein, all numerical values or numerical ranges include whole integers within or encompassing such ranges and fractions of the values or the integers within or encompassing ranges unless the context clearly indicates otherwise. Thus, for example, reference to a range of 80% or greater, includes any numerical value or range within or encompassing such values, such as 81%, 82%, 83%, 84%, 85%, 86%, 87%, etc., as well as 80.1, 81.1%, 81.2%, 81.30%, 81.4%, 81.5%, etc., and any numerical range within such a range, such as 80-82%, 80-85%, 85-88%, 86-88%, 89-95, 90-95%, 95-99%, etc.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described. Nevertheless, it will be understood that various modifications may be made without departing from the spirit and scope of the invention. Accordingly, the following examples are intended to illustrate but not limit the scope of invention described in the claims.

The examples set forth herein are illustrative of different compounds, products and conditions that can be used in practicing the embodiments. All proportions are by weight unless otherwise indicated. It will be apparent, however, that the embodiments can be practiced with many types of compositions and can have many different uses in accordance with the disclosure above and as pointed out hereinafter.

EXAMPLES

Example 1

A 5 L round bottom flask equipped with magnetic stirring was flame-dried and cooled under argon. Acetonitrile (1.5 L) and trifluoroacetic anhydride (358 mL, 2.58 mol) were combined. A solution of imidazole (84 g, 1.23 mol) in acetonitrile (500 mL) was added drop-wise over approximately 40 min and the mixture was heated to reflux and monitored by HPLC. Once all of the imidazole was consumed (2.5 h) tetraphenyl-biphenyldiamine (TBD) (100 g, 0.20 mol) was added and the resulting yellow suspension was stirred at reflux for 16 h. HPLC showed no unreacted TBD remained. The reaction was poured into 2.5 L of ice/water and stirred for 1 h. A yellow precipitate was isolated by filtration (yield: 450 g—wet weight before drying).

Example 2

The imidazolium bistrifluoroacetate may be generated in situ in the presence of the tetraaryldiamine, obviating the step of pre-forming the reagent. To a two neck 2 L round bottom flask was added TBD (50 g, 0.102 mol), imidazole (34.9 g, 0.501 mol), followed by 900 mL of acetonitlle. The reaction was magnetically stirred and flask outfitted with a reflux condenser and purged with nitrogen. Trifluoroacetic anhydride (138 mL, 0.99 mol) was added over the course of 5 min. After addition of trifluoroacetic anhydride the reaction was set to reflux for 16 hours. HPLC showed no unreacted TBD remained. Reaction was poured into 3 L rapidly stirred water to evolve a yellow powder. This was filtered off and the filter cake washed with water until filtrate was clear and colorless. Obtained 170 g (wet weight before drying).

Example 3

The wet polyimidazoline product from imidazoline addition step (450 g—wet mass-assume 313 g, 100% yield from previous reaction) was dissolved in 1500 mL THF. HCl (1310 mL, 2.5 M aq—prepared by adding 273 mL of concentrated HCl to 1037 mL H$_2$O) was added and the reaction was heated to reflux and monitored by HPLC. Additional THF (500 mL) was added after the reaction reached reflux. The reaction was stirred at reflux overnight (16 h). HPLC showed no starting material remained (only one peak in chromatogram). The reaction was cooled to ambient temperature and an orange solid formed. The reaction mixture was filtered to afford the crude product as an orange solid (210 g—wet).

$^1$H NMR (CDCl$_3$, 300 MHz): product (single aldehyde peak & aromatic region suggest only one symmetrical compound was formed) and diamide resulting from hydrolysis of imidazoline (peak @δ=4.73 ppm) is present.

By-product (peak at δ=4.73 ppm) was removed by triturating the filter cake in 800 mL toluene at room temperature. Upon filtering a significant amount of water was evident in the orange filtrate (solid becomes more yellow). The material was triturated a second time (400 mL PhMe) and the filter cake washed with 500 mL toluene. $^1$H NM shows complete removal. Purity (HPLC)>99%. Yield 91 g as a 1:1 adduct with toluene.

Example 3

Alternatively, hydrolysis of imidazoline product can be conducted as follows. To a three necked round bottom flask was placed wet polyimidazoline product (170 g), THF (1275 mL) followed by 2.5 M HCl (660 mL). The resulting solution was magnetically stirred, flask outfitted with reflux condenser, and stoppers, and the reaction set to reflux for 16 h. HPLC analysis of the reaction demonstrated that all imidazoline was consumed. Reaction was stopped and left to cool to room temperature. Upon cooling the tetraformylated product precipitates from the reaction mixture, which was filtered off and washed with water, and then toluene to yield 55 g of the pure product.

Example 4

Alternatively both steps of the process can be performed in a single reaction vessel without isolation of the imidazolium intermediate. A 5 L round bottom flask equipped with mechanical stirring was flame-dried and cooled under Ar. Acetonitrile (800 mL), imidazole (79 g, 115 mmol), N,N'-diphenyl-N,N'-bis(3-methylphenyl)benzidine (mTBD) (100 g, 192 mmol), and trifluoroacetic anhydride (323 mL, 233 mmol) were combined and the mixture was heated to reflux and monitored by HPLC. The reaction was complete in less than 1.5 h to form the tetrasubstituted imidazoline product. The reaction mixture was removed from the oil bath and THF (1.6 L) and HCl (2 M aq, 800 mL) was added. The mixture was returned to the heating bath and stirred at 90 C for 16 h. No starting material remained with the tetrasubstituted imidazoline compound fully hydrolyzed to the tetraformyl product. The mixture was cooled to room temperature, diluted with MeOH (500 mL, drop-wise) and slowly poured into 4 L of water. This mixture was filtered to obtained a rust-coloured solid which contained byproducts. The mixture was dissolved in THF (1.2 L) and added drop-wise to a mixture of MeOH/water (5 L, 1:1). The resulting yellow solid was collected by filtration (144 g as wet solid). The sample was further purified by dissolving in toluene and filtering through a celite plug. All pure material was eluted from the plug by subsequent elution with THF. The product was obtained as adducts of toluene and THF. Taking into account the mass of included solvent in the purified product the total mass obtained was 85 g.

Example 5

A 5 L round bottom flask equipped with mechanical stirring was flame-dried and cooled under Ar. Acetonitrile (800 mL), imidazole (79 g, 116 mmol), N,N-diphenylbiphenyl-4-amine (150 g, 467 mmol), and trifluoroacetic anhydride (324 mL, 233 mmol) were combined and the mixture was heated to reflux and monitored by HPLC. The reaction was complete in about 2 h yielding the disubstituted imidazoline product. The heating mantel was turned off and THF (1.6 L) and HCl (2 M aq, 600 mL) were added. The heating mantel was turned on and set at 90 C and the mixture was stirred for 16 h. No polyimidazoline intermediate material remained yielding the diformylated product.

Example 6

A three necked, 3 L round bottom flask equipped with mechanical stirring was flame-dried and cooled under Ar. Acetonitrile (1150 mL) and trifluoroacetic anhydride (250 mL, 1.8 mol) were combined. Imidazole (59.2 g, 870 mmol) was added in portions and the mixture was heated to reflux and monitored by HPLC. Once all of the imidazole was consumed (~2.5 h) N,N'-diphenyl-N,N'-bis(4-methylphenyl)benzidine (p-TBD) (20.8 g, 40.2 mmol) was added and the resulting yellow suspension was stirred at reflux for 2 h. HPLC showed no starting material remained and only one new peak corresponding to the disubstituted imidazoline product. The reaction was cooled to room temperature and stirred overnight. The reaction mixture was diluted with MeOH (500 mL) and slowly poured into water (1000 mL) to afford a yellow precipitate of the solid product having a wet mass of 301 g.

What is claimed is:
1. A compound having structure II:

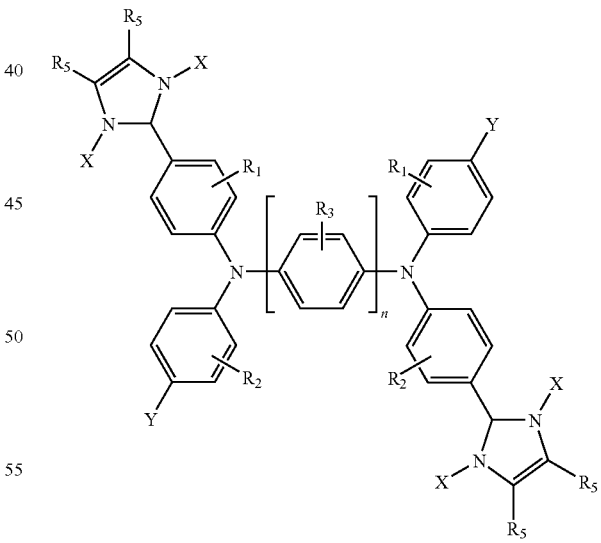

(II)

wherein:
X is selected from the group consisting of trifluoroacetyl, trifluoromethanesulfonyl, trichloroacetyl, trichloromethanesulfonyl, tribromoacetyl, tribromomethanesulfonyl, acetyl, methanesulfonyl, tolylsulfonyl, and mesitylsulfonyl;
Y is selected from the group consisting of $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl and imidazoline having structure:

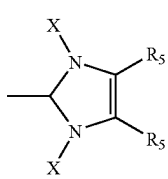

wherein:
$R_5$ is selected from the group consisting of hydrogen, $C_1$-$C_5$ alkyl, $C_3$-$C_7$ cyclic alkyl, halogen, nitro, alcohol, amide, and amine, or two adjacent $R_5$ moieties on the same imidazole represent a fused benzene ring, thus forming a benzimidazole optionally substituted with $C_1$-$C_5$ alkyl, $C_3$-$C_7$ cyclic alkyl, halogen, nitro, alcohol, amide, and amine;
$R_1$, $R_2$, and $R_3$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, and aryl optionally substituted with $C_1$-$C_5$ alkyl;
$R_4$ is selected from the group consisting of $C_1$-$C_5$ alkyl, $C_3$-$C_7$ cyclic alkyl, hydroxy, ω-hydroxy substituted $C_2$-$C_8$ alkyl, halogen, aryl, and aryl optionally substituted with $C_1$-$C_5$ alkyl;
n=1 to 3.

2. The compound of claim 1 selected from the group consisting of:

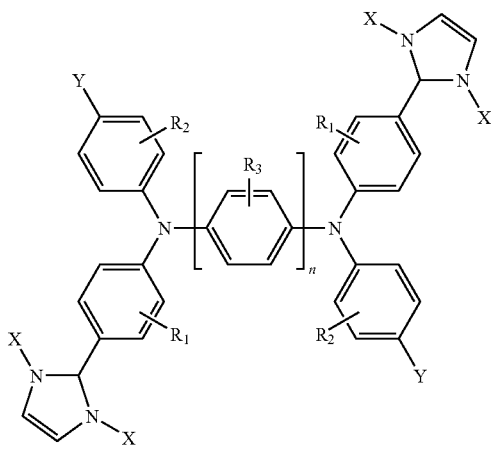

wherein:
X is selected from the group consisting of trifluoroacetyl, trifluoromethanesulfonyl, trichloroacetyl, trichloromethanesulfonyl, tribromoacetyl, tribromomethanesulfonyl, acetyl, methanesulfonyl, tolylsulfonyl, and mesitylsulfonyl;
Y is selected from the group consisting of $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, and aryl optionally substituted with $C_1$-$C_5$ alkyl;
$R_1$, $R_2$, and $R_3$ are each independently hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, and aryl optionally substituted with $C_1$-$C_5$ alkyl;
$R_4$ is aryl, optionally substituted with $C_1$-$C_5$ alkyl; and
n=1 to 3.

3. The compound of claim 2, having structure:

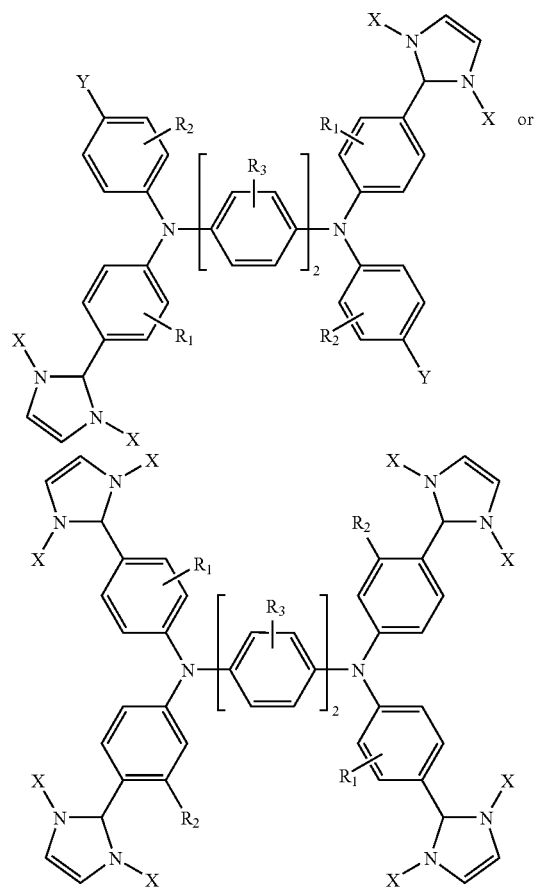

wherein:
X is trifluoroacetyl;
Y is $C_1$-$C_5$ alkyl or aryl optionally substituted with $C_1$-$C_5$ alkyl;
$R_1$, $R_2$, $R_3$, and $R_4$ are each independently hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, and aryl optionally substituted with $C_1$-$C_5$ alkyl.

4. A compound selected from the group consisting of:

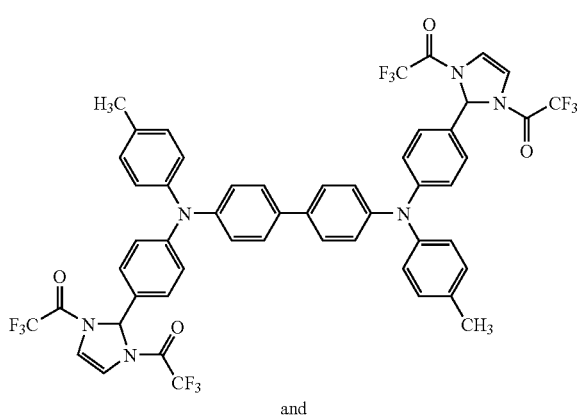

and

-continued

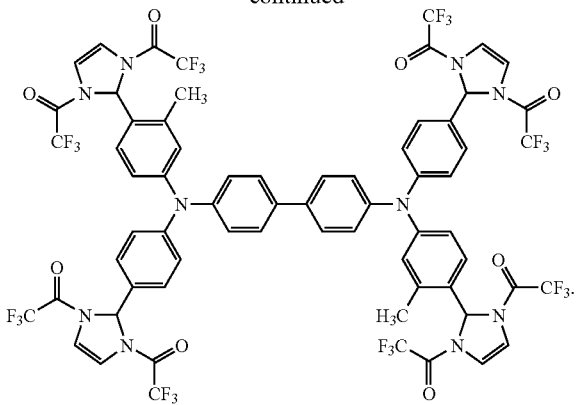

5. A process comprising the steps of:
(a) charging a vessel with a mixture comprising imidazole, an acyl or sulfonyl anhydride, and one of a compound having the following structures A or B respectively:

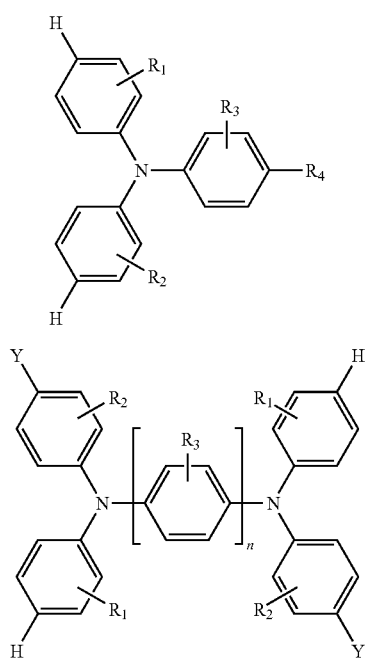

wherein
Y is selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl;
$R_1$ $R_2$, and $R_3$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl; and
$R_4$ is $C_1$-$C_5$ alkyl, $C_3$-$C_7$ cyclic alkyl, hydroxy, ω-hydroxy substituted $C_1$-$C_8$ alkyl, halogen, aryl optionally substituted with $C_1$-$C_5$ alkyl; and
n=1 to 3;

(b) heating the mixture in a non aqueous solvent until the compound A or B is consumed; and
(c) quenching the reaction with water to precipitate a polyimidazoline product.

6. The process of claim 5, wherein compound A has a structure:

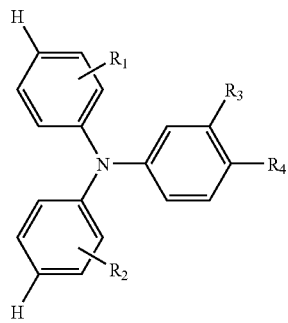

wherein:
$R_1$ $R_2$, and $R_3$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl; and
$R_4$ is aryl optionally substituted with $C_1$-$C_5$ alkyl.

7. The process of claim 5, wherein compound B has a structure:

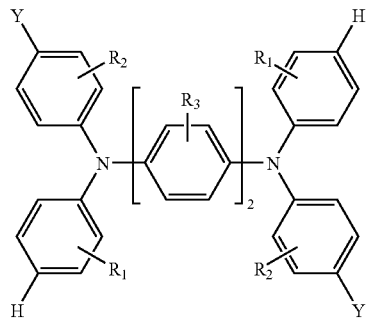

wherein:
Y, $R_1$, $R_2$, and $R_3$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl.

8. The process of claim 7, wherein compound B has a structure:

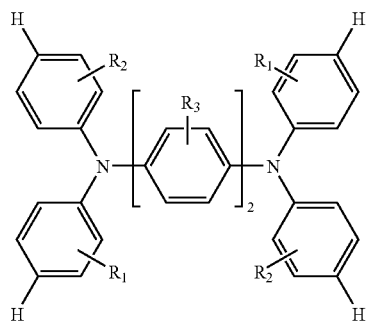

wherein:

$R_1$, $R_2$, and $R_3$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl.

9. The process of claim 8, wherein the compound A or B is selected from the group consisting of

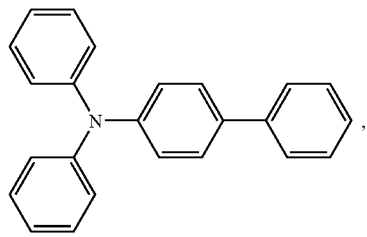
,

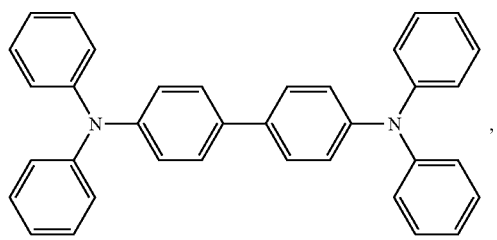
,

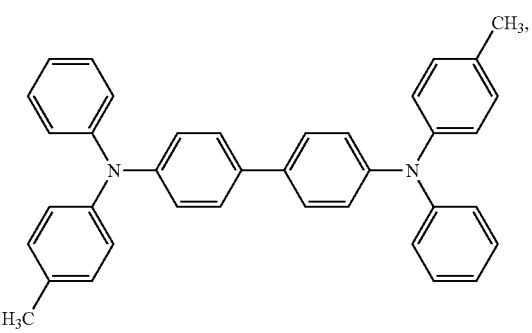

and

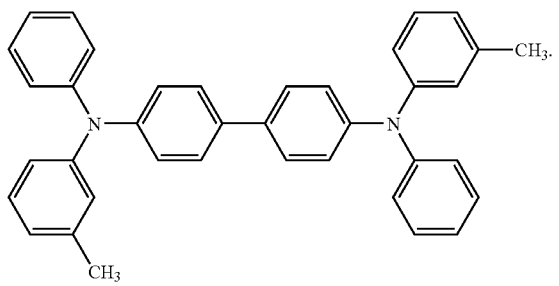

10. The process of claim 5, wherein the polyimidazoline product has a structure I or II:

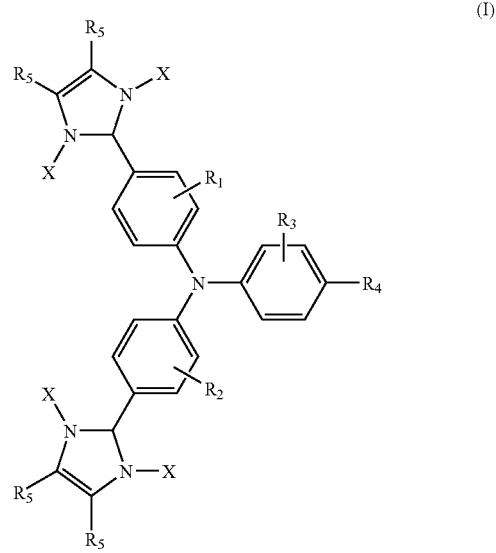
(I)

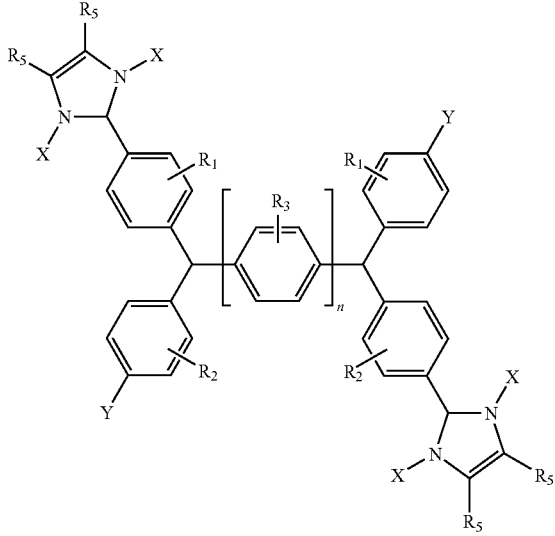
(II)

wherein:

X is selected from the group consisting of trifluoroacetyl, trifluoromethanesulfonyl, trichloroacetyl, trichloromethanesulfonyl, tribromoacetyl, tribromomethanesulfonyl, acetyl, methanesulfonyl, tolylsulfonyl, and mesitylsulfonyl;

Y is selected from the group consisting of $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl, and imidazoline having structure:

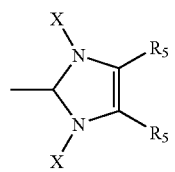

wherein:
R₅ is selected from the group consisting of hydrogen, $C_1$-$C_5$ alkyl, $C_3$-$C_7$ cyclic alkyl, halogen, nitro, alcohol, amide, and amine, or two adjacent R₅ moieties on the same imidazole represent a fused benzene ring, thus forming a benzimidazole optionally substituted with $C_1$-$C_5$ alkyl, $C_3$-$C_7$ cyclic alkyl, halogen, nitro, alcohol, amide, and amine;
R₁, R₂, and R₃ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, and aryl optionally substituted with $C_1$-$C_5$ alkyl;
R₄ is selected from the group consisting of $C_1$-$C_5$ alkyl, $C_3$-$C_7$ cyclic alkyl, hydroxy, ω-hydroxy substituted $C_2$-$C_8$ alkyl, halogen, aryl, and aryl optionally substituted with $C_1$-$C_5$ alkyl;
n=1 to 3.

11. The process of claim 5, wherein R₁, R₂, and R₃ are each hydrogen.

12. The process of claim 5, wherein one or more X is trifluoroacetyl.

13. The process of claim 5, wherein the polyimidazoline is a compound having a structure selected from the group consisting of:

14. The process of claim 5, wherein the heating of step b) is between 40 to 120° C.

15. The process of claim 5, wherein the non aqueous solvent of step b) is solvent selected from the group consisting of as tetrahydrofuran, diethylether, diisopropylether, dichloromethane, chloroform, acetonitrile, propionitrile, dioxane, dioxolane, tetrahydropyran, dimethoxyethane, glymes, nitromethane, ethyl acetate, propyl acetate, acetone, methylethylketone, methyl isobutyl ketone, acetic acid, trifluoroacetic acid, trifluoroacetic anhydride, acetic anhydride, and alkanes.

16. A process for making a polyformylated product comprising the steps of:
(a) charging a vessel with a mixture comprising imidazole, an acyl or sulfonyl anhydride, and one of a compound having the following structures A or B respectively:

-continued

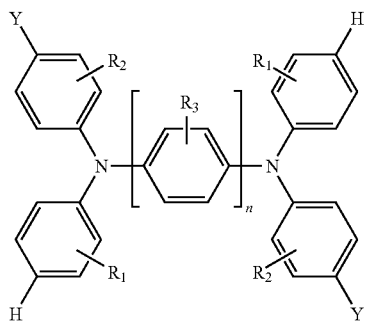

B wherein
- Y is selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl;
- $R_1$ $R_2$, $R_3$, and $R_4$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_5$ alkyl, halogen, and aryl optionally substituted with $C_1$-$C_5$ alkyl; and
- n=1 to 3;

(b) heating the mixture in a polar non aqueous solvent until the compound A or B is consumed;

(c) charging the vessel with an aqueous acid;

(d) heating the mixture in aqueous solvent system until polyimidazoline is consumed.

17. The process of claim 16, wherein compound A has a structure:

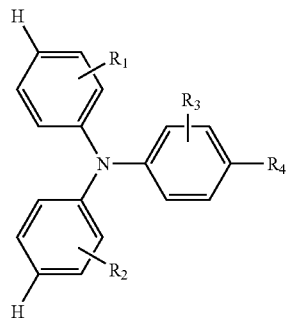

wherein:
- $R_1$, $R_2$, $R_3$, and $R_4$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, and aryl optionally substituted with $C_1$-$C_5$ alkyl.

18. The process of claim 16, wherein compound B has a structure:

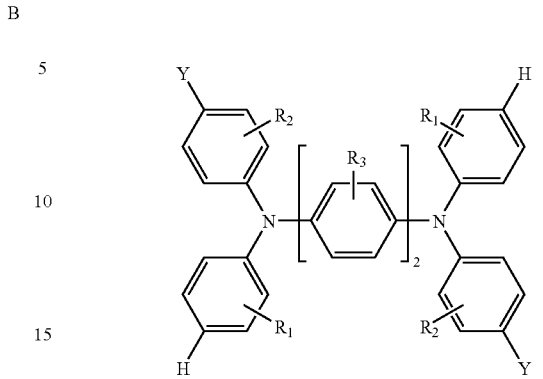

wherein:
- Y, $R_1$, $R_2$, and $R_3$ are each independently selected from the group consisting of hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen, aryl optionally substituted with $C_1$-$C_5$ alkyl.

19. The process of claim 16, wherein compound A or B is selected from the group consisting of:

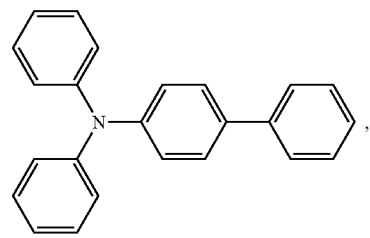

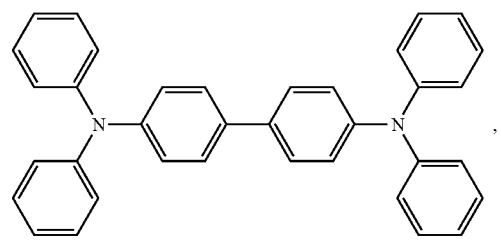

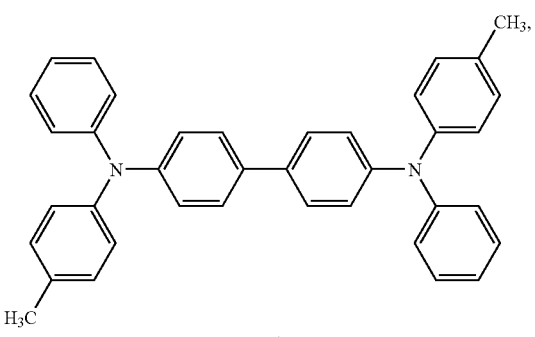

and

-continued

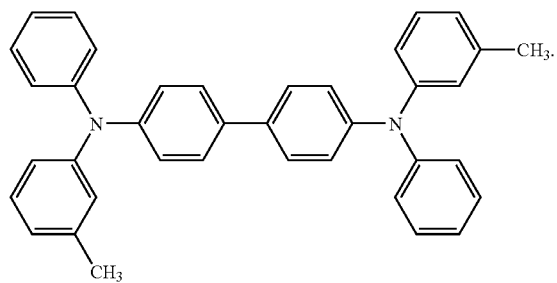

20. The process of claim 16, wherein the polyformylated product has a structure:

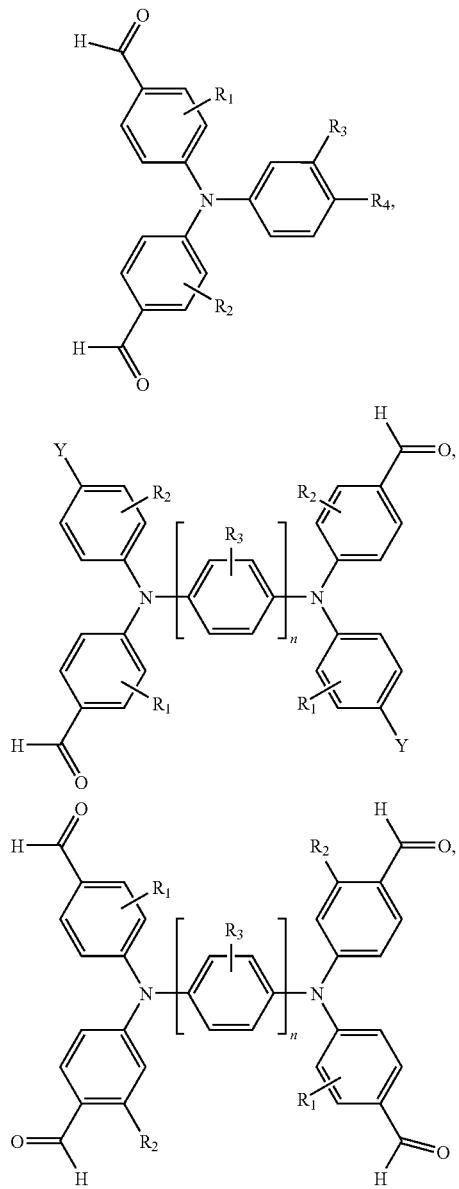

wherein:
Y, $R_1$, $R_2$, $R_3$, and $R_4$ are each independently selected from the group consisting of hydrogen, $C_1$-$C_5$ alkyl, $C_3$-$C_7$ cyclic alkyl, $C_1$-$C_4$ alkoxy, hydroxy, ω- hydroxy substituted $C_2$-$C_8$ alkyl, halogen, aryl optionally substituted with $C_1$-$C_5$ alkyl; and
n=1 to 3.

21. The process of claim 16, wherein the acyl is trifluoroacyl.

22. The process of claim 16 wherein the polyformylated product has a structure selected from the group consisting of:

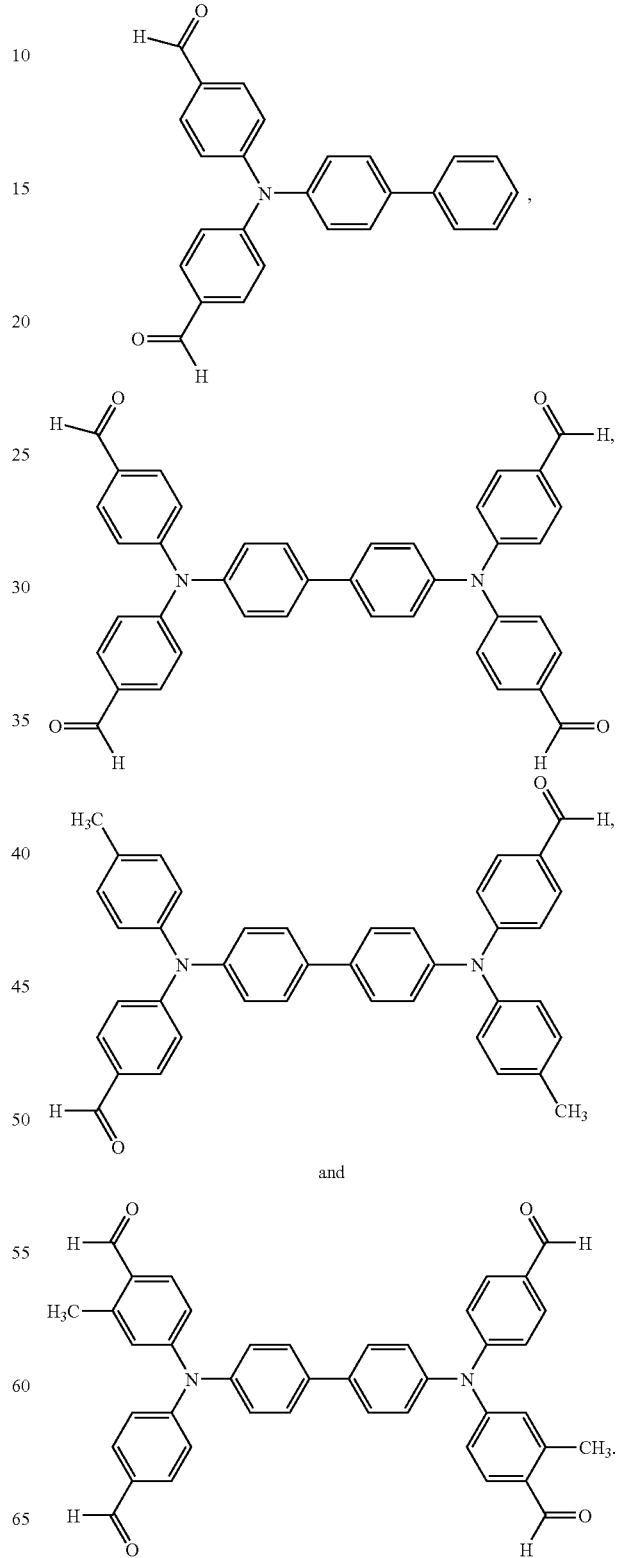

23. The process of claim 16, wherein the heating of step b) is between 40 to 120° C.

24. The process of claim 16, wherein the non aqueous solvent of step b) is selected from the group consisting of tetrahydrofuran, diethylether, diisopropylether, dichloromethane, chloroform, acetonitrile, propionitrile, dioxane, dioxolane, tetrahydropyran, dimethoxyethane, glymes, nitromethane, ethyl acetate, propyl acetate, acetone, methylethylketone, methyl isobutyl ketone, acetic acid, trifluoroacetic acid, trifluoroacetic anhydride, acetic anhydride, and an alkane.

* * * * *